(12) United States Patent
Kopp et al.

(10) Patent No.: US 10,456,777 B2
(45) Date of Patent: Oct. 29, 2019

(54) PRESSURE TRANSMISSION LIQUID FOR CELLULAR ANALYZER, CELLULAR ANALYZER AND METHOD FOR ANALYZING A LIQUID CELLULAR SAMPLE

(71) Applicant: Roche Diagnostics Operations, Inc., Indianapolis, IN (US)

(72) Inventors: Martin Kopp, Huenenberg See (CH); Emad Sarofim, Hagendorn (CH)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 461 days.

(21) Appl. No.: 15/099,644

(22) Filed: Apr. 15, 2016

(65) Prior Publication Data

US 2016/0303556 A1     Oct. 20, 2016

(30) Foreign Application Priority Data

Apr. 17, 2015   (EP) .................................. 15164009

(51) Int. Cl.
  *B01L 3/02*      (2006.01)
  *G01N 35/10*    (2006.01)
(52) U.S. Cl.
  CPC ............ *B01L 3/0217* (2013.01); *B01L 3/021* (2013.01); *G01N 35/1016* (2013.01);
  (Continued)
(58) Field of Classification Search
  CPC combination set(s) only.
  See application file for complete search history.

(56) References Cited

U.S. PATENT DOCUMENTS

| 4,818,492 A | 4/1989 | Shimizu |
| 6,203,759 B1 * | 3/2001 | Pelc ...................... B01L 3/0265 222/333 |

(Continued)

FOREIGN PATENT DOCUMENTS

| EP | 2012129 A1 | 1/2009 |
| EP | 2193848 A1 | 6/2010 |

(Continued)

OTHER PUBLICATIONS

Haynes, W. M., Editor-in-Chief, Electrical Conductivity of Aqueous Solutions, CRC Handbook of Chemistry and Physics Internet Version, 2016, p. 5-73.

*Primary Examiner* — Brian R Gordon
(74) *Attorney, Agent, or Firm* — Woodard, Ernhardt, Henry, Reeves & Wagner, LLP

(57) ABSTRACT

A pressure transmission liquid for a cellular analyzer, a system for transferring a liquid cellular sample for analysis by a cellular analyzer, and a method for transferring a liquid cellar sample for analysis are disclosed. The pressure transmission liquid includes an aqueous solution which is isotonic and substantially non-conductive characteristics. The cellular analyzer includes a pipetting module having a pipetting tip, a device for positioning the pipetting module, a sensor for detecting a liquid level of a liquid cellular sample to be analyzed, a pressure transmission liquid, and a pressure transmission liquid conduit connected to the pipetting tip and the pressure transmission liquid reservoir.

6 Claims, 7 Drawing Sheets

(52) U.S. Cl.
CPC ... *B01L 2200/0684* (2013.01); *B01L 2200/14* (2013.01); *B01L 2300/12* (2013.01); *B01L 2300/14* (2013.01); *B01L 2300/163* (2013.01); *G01N 2035/1025* (2013.01)

(56) References Cited

U.S. PATENT DOCUMENTS

| | | | | |
|---|---|---|---|---|
| 6,551,558 | B1 * | 4/2003 | Mann | G01F 23/24 116/109 |
| 6,858,439 | B1 * | 2/2005 | Xu | B01J 19/0046 204/409 |
| 8,030,093 | B2 | 10/2011 | Hayashi et al. | |
| 2003/0110840 | A1 * | 6/2003 | Arriaga | G01N 15/1404 73/61.72 |
| 2005/0186281 | A1 * | 8/2005 | Lalum | A01N 31/08 424/487 |
| 2007/0135343 | A1 * | 6/2007 | Webb | A61K 9/0019 424/680 |
| 2008/0268542 | A1 * | 10/2008 | Rubio | C12N 15/87 435/461 |
| 2009/0082438 | A1 * | 3/2009 | Kataoka | A61K 31/282 514/492 |
| 2012/0282703 | A1 * | 11/2012 | Tang | C12Q 1/54 436/95 |
| 2014/0127078 | A1 * | 5/2014 | Morikawa | A61L 2/18 422/29 |
| 2014/0216935 | A1 * | 8/2014 | Vezenov | B03C 5/005 204/547 |
| 2014/0322101 | A1 | 10/2014 | Saito et al. | |
| 2014/0322333 | A1 * | 10/2014 | Stadler | B82Y 30/00 424/489 |
| 2016/0193613 | A1 * | 7/2016 | Walti | B03C 5/005 |
| 2016/0331697 | A1 * | 11/2016 | Sandford | A61K 9/10 |

FOREIGN PATENT DOCUMENTS

| | | |
|---|---|---|
| EP | 2246704 A1 | 11/2010 |
| EP | 2607905 A1 | 6/2013 |

* cited by examiner

PRESSURE TRANSMISSION LIQUID FOR CELLULAR ANALYZER, CELLULAR ANALYZER AND METHOD FOR ANALYZING A LIQUID CELLULAR SAMPLE

CROSS-REFERENCE TO RELATED APPLICATIONS

This application claims the benefit of European Patent Application No. 15164009.1 filed Apr. 17, 2015, the disclosure of which is hereby incorporated by reference in its entirety.

TECHNICAL FIELD

The disclosure relates to automated handling of fluid samples and, more particularly, to a pressure transmission liquid for a cellular analyzer, a cellular analyzer and a method for analyzing a liquid cellular sample.

BACKGROUND

In consideration of the fact that there is an ongoing increase in chemical, biochemical and genetic analysis in assays, a strong demand for the automated pipetting of liquid cellular samples can be observed.

Different types of pipetting units and pipetting methods have been implemented in various analytical instruments. Among the various pipetting methods, the most challenging ones are those requiring aspirating a volume of test liquid through a cap of a test liquid container. This is typically done by piercing with the nozzle of the pipetting unit a septum of elastomeric material sealing a test liquid container in which the test liquid is contained. Precision of volume and reproducibility may be particularly hard to achieve when the test liquid container is partially evacuated and/or the volume to be aspirated is small, e.g., below 5-10 microliters. This is due to the fact that air may be present in the pipetting unit and also to the fact that negative pressure, i.e., a pressure lower than atmospheric pressure, is present in the liquid container. This negative pressure, which may be different from container to container, may have an effect on the air in the pipetting unit. This in turn may affect the actual volume of liquid being aspirated and the position of the aspirated volume in the pipetting unit. This means that a first pipetting error may occur when aspirating (a wrong volume) and a second pipetting error may occur when dispensing (wrong position), possibly resulting in only part of the aspirated test liquid being dispensed or no test liquid at all being dispensed.

In order to improve precision of pipetting, the pipetting unit may be operated with a pressure transmission liquid, in which the presence of air in the pipetting unit is minimized. However, a small amount of air may be still dispersed in the pressure transmission liquid, e.g., in the form of microbubbles. Air is typically present also at the extremity of the nozzle, e.g., due to evaporation of pressure transmission liquid or on purpose by aspirating a plug of air in order to separate the pressure transmission liquid from the test liquid to be aspirated. This air, which is affected by the pressure conditions inside the container, may be the major responsible factor for pipetting errors especially for small volumes as mentioned above.

Nowadays automated cellular analyzers such as hematology analyzers, e.g., 3 or 5 part differential hematology analyzers, or other analyzers and pipetting robots pipetting cellular samples need to pipette cellular samples precisely, accurately, safely and contamination free. Such cellular samples are, e.g., blood, diluted blood, processed blood products, other body fluids containing cells such as suspensions of cells received from bone marrow, cerebrospinal fluid (CSF), urine, suspensions of cells received from smears, or other cell preparations or cell culture media containing cellular matter. Such cellular samples are often held, provided and processed in tubes or other suitable containers, such as, e.g., capped or uncapped blood collection tubes, plastic tubes, coated glass tubes, etc.

As, on one hand, the pipetting and pressure transmission liquid, on such automated analyzers, is done under full control of the automat and is generally unattended by a human user, and on the other hand, such analyzers produce in many cases results which are critical, such as a health status of a person, the safe, reliable, accurate, precise and cross-contamination-free operation is a must. An efficient means to support this is the use of capacitive level detection. As a capacitive level detection, a means which is able to detect the upper surface of a sample is to be understood, which helps the analyzers to locate the sample's upper level and consecutively conduct a safe, precise and accurate pipetting while taking into consideration the upper and lower level of the sample. Anyhow, many cellular analyzers do not use such means. Some analyzers use a fixed immersion depth for the pipetting tip. In such systems, often only a completely absent sample is detected. Other analyzers that use capacitive level detections use as pressure transmission liquid deionized water, which is not compatible with cellular samples, leading to lysis of cells under the hypotonic conditions at the interface of the sample and the pressure transmission liquid. Other analyzers using liquid level detections use isotonic solutions of ionic components that are prone to electromagnetic disturbances, which can cause errors in finding the upper level of the sample.

The use of different liquids in the pipetting unit is rather complicated, particularly in view of the liquid level detection by means of catching the variance of capacitance.

BRIEF SUMMARY

It is against the above background that the embodiments of the present disclosure provide certain unobvious advantages and advancements over the prior art. In particular, the inventors have recognized a need for improvements in pressure transmission liquid for a cellular analyzer, a cellular analyzer, and a method for analyzing a liquid cellular sample using a pressure transmission liquid.

Although the embodiments of the present disclosure are not limited to specific advantages or functionality, it is noted that the present disclosure provides methods that are simplified and fulfill the requirements of being cell compatible and providing significantly less electronic noise caused by the pipetting tip. With other words, the present disclosure provides a pressure transmission liquid, a cellular analyzer, and a method for analyzing a cellular sample allowing a precise, reliable and accurate detection of the cellular sample and subsequent pipetting transfer of an aliquot of such a sample.

In accordance with one embodiment of the present disclosure, a pressure transmission liquid is provided comprising an aqueous solution of at least one substance, wherein the solution has isotonic and substantially non-conductive characteristics.

In accordance with another embodiment of the present disclosure, a cellular analyzer is provided comprising a pipetting module having a pipetting tip, an automated positioning device configured for positioning the pipetting module, a capacitive liquid level sensor configured for detecting a liquid level of a liquid cellular sample to be analyzed, a pressure transmission liquid reservoir comprising a pressure transmission liquid according to an embodiment of the instant disclosure, and a pressure transmission liquid conduit connected to the pipetting tip and the pressure transmission liquid reservoir.

In accordance with yet another embodiment of the present disclosure, a method for analyzing a liquid cellular sample using a cellular analyzer according to an embodiment of the instant disclosure is provided, the method comprising positioning the pipetting tip at or in the vicinity of the liquid cellular sample, detecting a liquid level of the liquid cellular sample, immersing the pipetting tip into the liquid cellular sample, and transferring a negative pressure to the pipetting tip so as to aspirate an aliquot of the liquid cellular sample into the pipetting tip.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Figure 1:
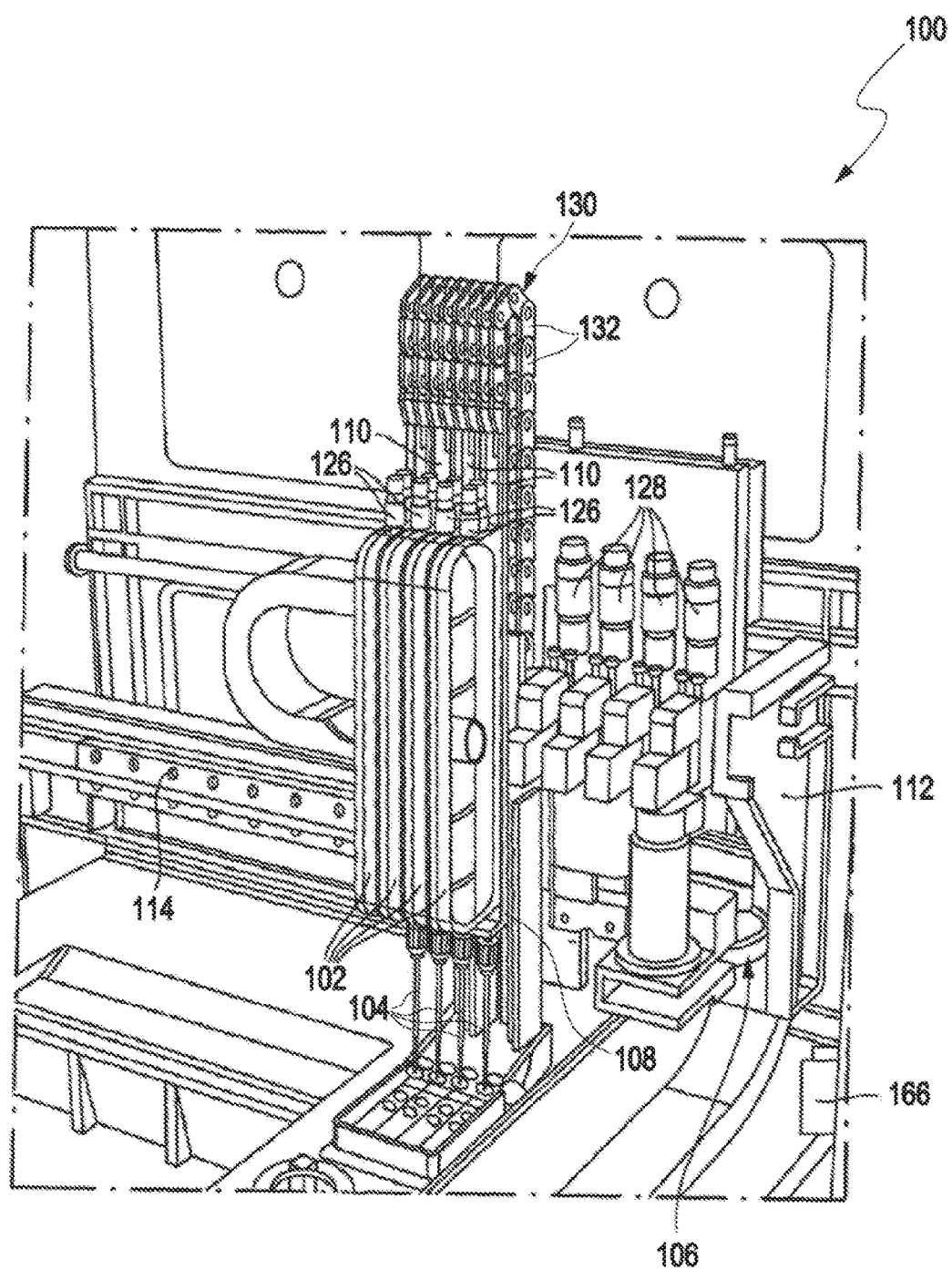
FIG. 1 shows a schematic perspective view of an exemplary embodiment of a cellular analyzer according to the present disclosure.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

In accordance with one embodiment of the present disclosure, a pressure transmission liquid for a cellular analyzer is provided. A pressure transmission liquid in the sense of the present disclosure is a liquid adapted to be used within a pipetting unit of a cellular analyzer and a respective pressure transmission liquid conduit connected thereto. Such a pressure transmission liquid is used to provide a positive pressure or a negative pressure in the pipetting unit in order to either dispense from or to suck a liquid into the pipetting unit. The pressure transmission liquid comprises an aqueous solution of at least one substance, wherein the solution has isotonic and substantially non-conductive characteristics. The term "isotonic" in the sense of the present disclosure is to be understood in that the solution has the same osmolarity as the sample or cells to be analyzed by the cellular analyzer. In the field of the present disclosure, i.e., the analysis of cellular samples, it is typical that the pressure transmission liquid has an osmolarity of 150 mOsm/l to 600 mOsm/l. The term "substantially non-conductive" in the sense of the present disclosure is to be understood in that the solution basically has an electrical conductivity below a critical threshold of electric noise occurring during detection of variation of capacitance such that the solution allows a clear detection of the variation of capacitance. As the electrical conductivity is caused by ions, the solution has ionic characteristics below a critical threshold of electric noise occurring during detection of variation of capacitance. With other words, the solution comprises ions up to an amount that does not disturb the detection of the level of the liquid cellular sample based on the detection by means of a variation of capacitance. Thus, the solution has an electrical conductivity below a certain threshold. In the field of the present disclosure, it is typical that the solution has an electrical conductivity of not more than 2 mS/cm. As the characteristics of the solution are influenced by the characteristics of the at least one substance, the at least one substance may have non-ionic, zwitter-ionic or low-ionic characteristics. As the solution has isotonic and substantially non-conductive characteristics, the pressure transmission liquid is cell compatible and provides significantly low electronic noise caused by the pipetting tip.

In order to provide the isotonic characteristics, the at least one substance may comprise a carbohydrate or a derivative thereof at a corresponding concentration. For example, the at least one substance may comprise at least one element selected from the group consisting of: a monosaccharide, disaccharide, oligosaccharide, an ester thereof and an ether thereof. The at least one substance may alternatively or in addition comprise at least one element selected from the group consisting of: sorbitol, glucose, sucrose, fructose, lactose, hexose and pentose. Thus, it is ensured that the pressure transmission liquid is cell compatible and does not lead to lysis of any cells.

In order to provide the substantially non-conductive characteristics, the at least one substance may comprise an amino acid, wherein the solution has a pH at which the amino acid is substantially at its isoelectric point. For example, the amino acid may be glycine, alanine or betaine (trimethyl glycine).

As mentioned above, the at least one substance may comprise some ionic components. In this case, the solution has an electrical conductivity of not more than 2 mS/cm, more typically not more than 1 mS/cm, and most typically not more than 0.5 mS/cm. The ionic components may comprise at least one element selected from the group consisting of: ions of alkali or earth alkali metals, halides, copper phosphates, sulfates, borates, nitrates, carbonates, azide, amino-acids, and ions of organic acids, benzoate, and salts of EDTA. Such minor ionic components may be added to adjust the residual conductivity, adjust pH, may be added as complex former, as antimicrobial agent, or for other purposes such as in order to support the downstream analysis. For example, in cases where the downstream analysis bases on the coulter-counter principle or other principle requiring some conductivity, the electrical conductivity is from 0.1 mS/cm to 2 mS/cm.

The solution may further comprise at least one antimicrobial preservative. For example, the antimicrobial preservative may be sodium azide or phenoxy-ethanol. Thus, a microbial deterioration of the pressure transmission liquid may be prevented.

According to the present disclosure, a cellular analyzer is disclosed. The cellular analyzer comprises a pipetting module having a pipetting tip, an automated positioning device for positioning the pipetting module, a capacitive liquid level sensor for detecting a liquid level of a liquid cellular sample to be analyzed, a pressure transmission liquid reservoir comprising a pressure transmission liquid as described before, and a pressure transmission liquid conduit connected to the pipetting tip and the pressure transmission liquid reservoir. Thus, the cellular analyzer may reliably detect a liquid level of the cellular sample and prevent any deterioration of the sample such as lysis.

The capacitive liquid level sensor may be adapted to detect the liquid level of the liquid cellular sample to be analyzed by means of a variation of capacitance. Thus, the liquid level may be detected with a well established method.

The cellular analyzer may further comprise a pump arranged within or in fluidic connection to the pressure transmission liquid conduit, wherein the pump is adapted to selectively transfer a negative pressure or a positive pressure to the pipetting tip. Thus, the pipetting process may be simplified and automated.

According to the present disclosure, a method for analyzing a liquid cellular sample using a cellular analyzer as described before is disclosed.

The method comprises the steps:
  positioning the pipetting tip at or in the vicinity of the liquid cellular sample,
  detecting a liquid level of the liquid cellular sample,
  immersing the pipetting tip into the liquid cellular sample, and
  transferring a negative pressure to the pipetting tip so as to aspirate an aliquot of the liquid cellular sample into the pipetting tip.

Thus, a liquid level of the cellular sample may be reliably detected while any deterioration of the sample such as lysis is prevented.

Summarizing the findings of the present disclosure, the following embodiments are typical:

Embodiment 1

Pressure transmission liquid for a cellular analyzer, comprising an aqueous solution of at least one substance, wherein the solution has isotonic and substantially non-conductive characteristics.

Embodiment 2

Pressure transmission liquid according to embodiment 1, wherein the at least one substance has non-ionic, zwitter-ionic or low-ionic characteristics.

Embodiment 3

Pressure transmission liquid according to embodiment 1 or 2, wherein the solution has an osmolarity of 150 mOsm/l to 600 mOsm/l and, more typically, from 200 mOsm/l to 450 mOsm/l.

Embodiment 4

Pressure transmission liquid according to any one of embodiments 1 to 3, where in the at least one substance comprises a carbohydrate or a derivative thereof.

Embodiment 5

Pressure transmission liquid according to embodiment 4, wherein the at least one substance comprises at least one element selected from the group consisting of: a monosaccharide, disaccharide, oligosaccharide, an ester thereof and an ether thereof.

Embodiment 6

Pressure transmission liquid according to any one of embodiments 1 to 5, where in the at least one substance comprises an amino acid, and wherein the solution has a pH at which the amino acid is substantially at its isoelectric point.

Embodiment 7

Pressure transmission liquid according to embodiment 6, wherein the amino acid is glycine, alanine or betaine.

Embodiment 8

Pressure transmission liquid according to any one of embodiments 1 to 7, where in the at least one substance comprises at least one element selected from the group consisting of: sorbitol, glucose, sucrose, fructose, lactose, hexose and pentose.

Embodiment 9

Pressure transmission liquid according to any one of embodiments 1 to 8, where in the solution has an electrical conductivity of not more than 2 mS/cm, more typically not more than 1 mS/cm, and most typically not more than 0.5 mS/cm.

Embodiment 10

Pressure transmission liquid according to embodiment 9, wherein the at least one substance comprises ionic components.

Embodiment 11

Pressure transmission liquid according to embodiment 10, wherein the ionic components comprise at least one element selected from the group consisting of: ions of alkali or earth alkali metals, halides, copper phosphates, sulfates, borates, nitrates, carbonates, azide, amino-acids, and ions of organic acids, benzoate, and salts of EDTA.

Embodiment 12

Pressure transmission liquid according to any one of embodiments 1 to 11, wherein the solution further comprises at least one antimicrobial preservative.

Embodiment 13

Pressure transmission liquid according to embodiment 12, wherein the antimicrobial preservative is sodium azide or phenoxy-ethanol.

Embodiment 14

A cellular analyzer comprising at least one pipetting module having a pipetting tip, an automated positioning device for positioning the pipetting module, a capacitive liquid level sensor for detecting a liquid level of a liquid cellular sample to be analyzed, a pressure transmission liquid reservoir comprising a pressure transmission liquid according to any one of embodiments 1 to 13, and a pressure transmission liquid conduit connected to the pipetting tip and the pressure transmission liquid reservoir.

Embodiment 15

The cellular analyzer according to embodiment 14, wherein the capacitive liquid level sensor is adapted to detect the liquid level of the liquid cellular sample to be analyzed by means of a variation of capacitance.

Embodiment 16

The cellular analyzer according to embodiment 14 or 15, further comprising a pump arranged within the pressure transmission liquid conduit, wherein the pump is adapted to selectively transfer a negative pressure or a positive pressure to the pipetting tip.

Embodiment 17

The cellular analyzer according to any one of embodiments 14 to 16, wherein the pipetting module comprises a fluid sample conduit for receiving fluid samples aspirated through the pipetting tip.

Embodiment 18

The cellular analyzer according to any one of embodiments 14 to 17, wherein the pressure transmission liquid conduit has at least one winding inside the pipetting module.

Embodiment 19

A method for analyzing a liquid cellular sample using a cellular analyzer according to any one of embodiments 14 to 18.

Embodiment 20

The method according to embodiment 19, comprising the steps:
positioning the pipetting tip at or in the vicinity of the liquid cellular sample,
detecting a liquid level of the liquid cellular sample,
immersing the pipetting tip into the liquid cellular sample, and
transferring a negative pressure to the pipetting tip so as to aspirate an aliquot of the liquid cellular sample into the pipetting tip.

Although the embodiments of the present disclosure are not limited to specific advantages or functionality, it is understood that one or more of the aforementioned embodiments of the disclosure may be combined as long as the combined embodiments are not mutually exclusive.

In order that the embodiments of the present disclosure may be more readily understood, reference is made to the following examples, which are intended to illustrate the disclosure, but not limit the scope thereof.

FIG. 1 shows a schematic perspective view of an exemplary embodiment of a cellular analyzer 100 according to the present disclosure. The cellular analyzer comprises at least one pipetting module 102. The pipetting module 102 comprises a pipetting tip 104. More particularly, the cellular analyzer 100 comprises a plurality of pipetting modules 102 as illustrated in FIG. 1. Accordingly, each of the pipetting modules 102 includes a pipetting tip 104. While a number of four pipetting modules 102 is illustrated in FIG. 1, it, however, is to be understood that more or fewer pipetting modules 102 can be used in accordance with specific demands for the pipetting of fluid samples.

The cellular analyzer 100 comprises an automated positioning device 106, which can be used to transfer the pipetting tip 104 with respect to cavities or vessels containing the fluid samples to be transferred and analyzed. Each pipetting module 102 is detachably mounted to a transfer head 108, which can be slidably moved in vertical direction along vertically extending vertical guiding rails 110, e.g., by means of a spindle drive. The vertical guiding rails 110 for guiding the transfer head 108 are fixed to a sliding carriage 112, which can be moved in two directions of travel in a horizontal plane using a two-rail translation system comprising two rails arranged in orthogonal relationship with respect to each other for moving the transfer head 108. In FIG. 1, one horizontal guiding rail 114 is illustrated. Since such a positioning system is well-known to those of skill in the art, it is not further detailed herein.

Figure 2:
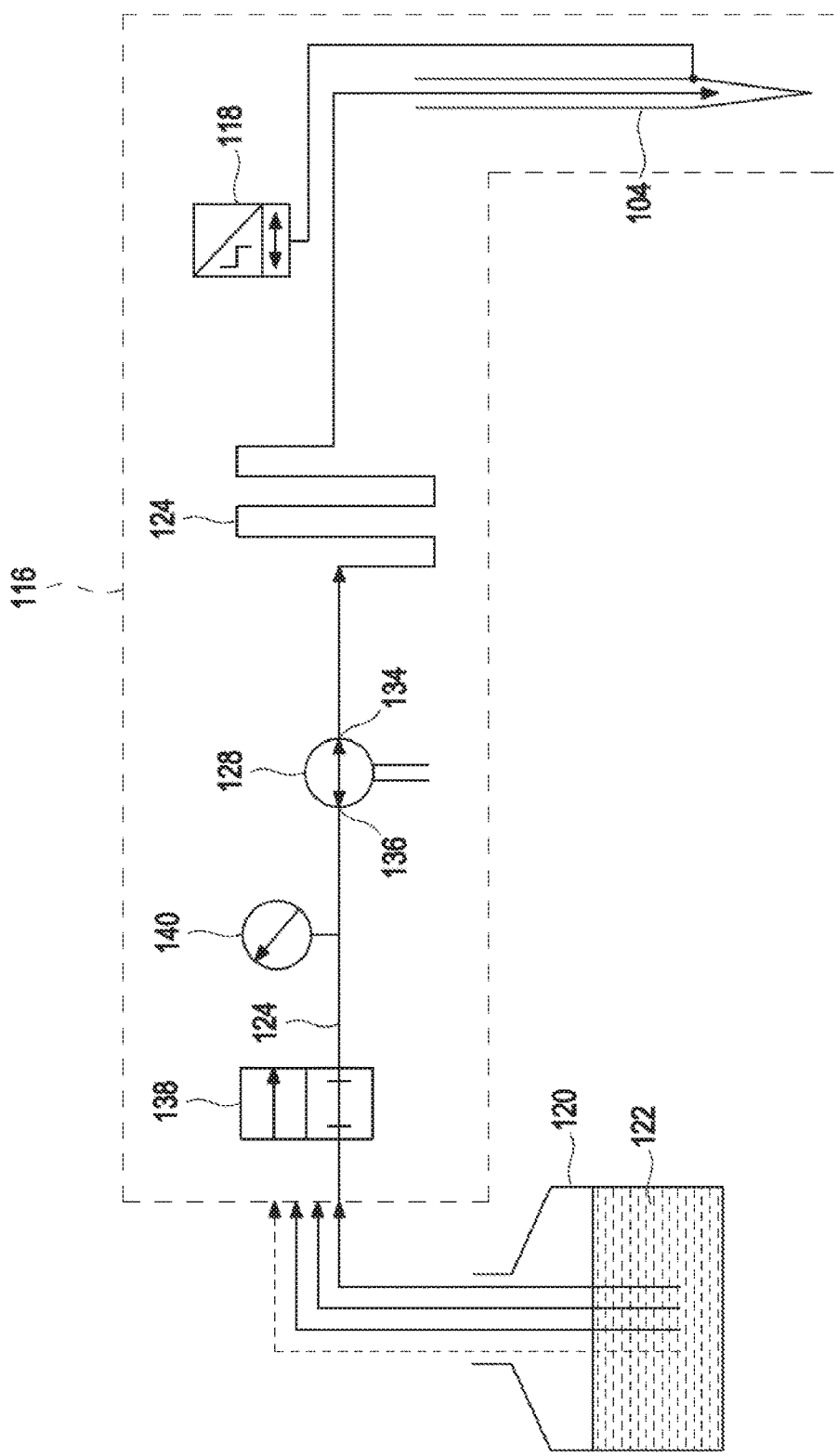
FIG. 2 shows a schematic diagram of a pipetting channel of the cellular analyzer.

Reference is now made to FIG. 2, illustrating a schematic diagram of a pipetting channel 116 including a pipetting module 102 of the cellular analyzer 100 used for the pipetting of fluid samples. The pipetting channel 116 is a functional entity for the pipetting of fluids including an individual pipetting module 102. Due to four pipetting modules 102, the cellular analyzer 100 has a number of four identical pipetting channels 116, each of which includes an individual pipetting module 102.

As can be taken from FIG. 2, the cellular analyzer 100 further comprises a capacitive liquid level sensor 118 for detecting a liquid level of a liquid cellular sample to be analyzed, a pressure transmission liquid reservoir 120 comprising a pressure transmission liquid 122 and a pressure transmission liquid conduit 124 connected to the pipetting tip 104 and the pressure transmission liquid reservoir 120 as will described in further detail below. The capacitive liquid level sensor 118 is adapted to detect the liquid level of the liquid cellular sample to be analyzed by means of a variation of capacitance.

More particularly, as shown in FIG. 1, the pipetting module 102 comprises a fluidic connector 126 fluidically connected to a pump 128 such as a piston, displacement or micro-gearwheel pump by the pressure transmission liquid conduit 124, which is guided by a separate metallic guiding chain 130 comprised of plural chain links 132 to mechanically protect the pressure transmission liquid conduit 124. Each pump 128 is fixed to the sliding carriage 112 and thus moves together with the sliding carriage 112 in a horizontal plane. Alternatively, the pumps 128 might be fixed to the transfer head 108. Each pump 128 is fluidically connected to the pressure transmission liquid reservoir 120 by means of the pressure transmission liquid conduit 124 (schematically illustrated in FIG. 2). Accordingly, an individual pipetting channel 116 of the cellular analyzer 100 including an individual pipetting module 102 comprises the pipetting tip 104 of the pipetting module 102, the pressure transmission liquid conduit 124 connecting the pipetting tip 104 with a first inlet/outlet port 134 of the pump 128, and the pressure transmission liquid conduit 124 connecting a second inlet/outlet port 136 of the pump 128 with the pressure transmission liquid reservoir 120. Thus, the pump 128 is arranged within the pressure transmission liquid conduit 124. Further, the pressure transmission liquid conduit 124 passes through a pressure transmission liquid valve 138 adapted to selectively open and close the pressure transmission liquid conduit 124, and is provided with a pressure sensor 140 for sensing of pressure transmission liquid pressure in the pressure transmission liquid conduit 124. The direction of flow within the pressure transmission liquid conduit 124 can be reversed in changing the driving direction of the pump 128.

The pump 128 for generating a positive or negative pressure in the pipetting tip 104 of each of the pipetting channels 116 is connected to the pressure transmission liquid reservoir 120 for at least partly filling the pressure transmission liquid conduit 124 (at least except for the fluid sample conduit 162) of the pipetting channel 116 with pressure transmission liquid. In case the pump 128 is located outside the cartridge 142, it can be typical to exclusively fill those parts of the pressure transmission liquid conduits 124, which are located outside the cartridge 142 with pressure transmission liquid 122.

In case the pump 128 is accommodated in the cavity 146 of the cartridge 142 of the pipetting module 102 to which it belongs, each of the pipetting channels 116 is a structural entity as identified by the pipetting module 102. In other words, each of the pipetting modules 102 may include all components of a pipetting channel 116 as illustrated in FIG. 2.

Figure 3:
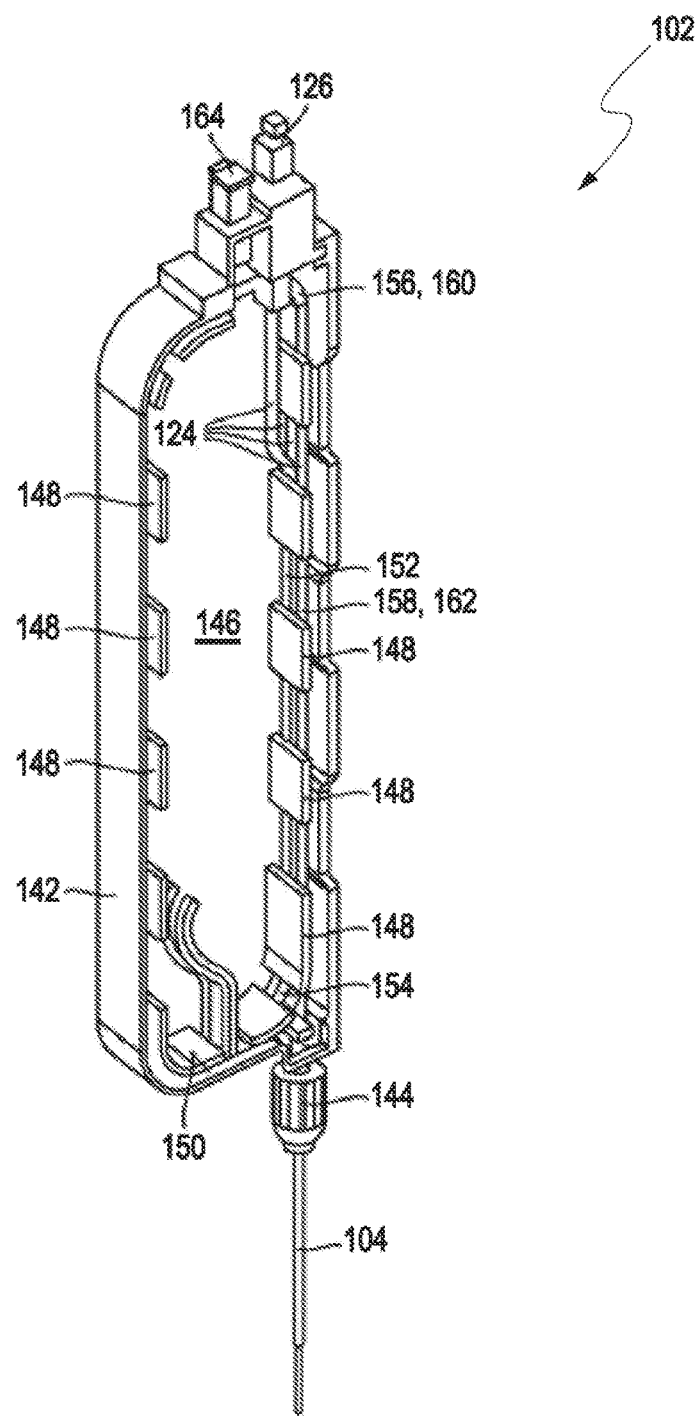
FIG. 3 shows a schematic perspective view of an exemplary embodiment of a pipetting module according to the present disclosure.

FIG. 3 shows a schematic perspective view of an exemplary embodiment of the pipetting module 102 according to the present disclosure. As explained above, the pipetting module 102 includes the re-usable pipetting tip 104, which is a needle for pipetting of fluid samples, the needle being fixed to an elongated hollow cartridge 142 by means of a threaded connection. The threaded connection is comprised of a threaded pin screwed into a threaded hole of the cartridge 142 (not further detailed in FIG. 3). A corrugated outer surface 144 at the cartridge sided end of the pipetting tip 104 facilitates turning of the pipetting tip 104 for screwing or unscrewing with cartridge 142. The pipetting tip 104 may thus be readily fixed or removed and replaced by another pipetting tip 104 as desired. In FIG. 3, the cartridge 142 is shown without side walls for the purpose of illustration only. Stated more particularly, the cartridge 142 is a closed housing aside from the screwed hole for fixing the pipetting tip 104 and the fluidic connector 126.

The pipetting tip 104, which is made of an electrically conductive material, particularly a metallic material, e.g., steel, is fluidically connected to the plastic-made pressure transmission liquid conduit 124 accommodated in a cavity 146 of the cartridge 142 for transferring a pump-generated negative or positive pressure to the pipetting tip 104. The cavity 146 of the cartridge 142 is provided with a plurality of guiding faces 148 arranged along an inner wall 150 of the cartridge 142 for guiding the pressure transmission liquid conduit 124. As supported by the guiding faces 148, the pressure transmission liquid conduit 124 winds three and a half times along the inner wall 150 of the cartridge 142 to be finally connected with the fluidic connector 126.

Due to a nearly rectangular, e.g., parallel-epipedic, shape of the cavity 146, the pressure transmission liquid conduit 124 has longer conduit portions 152 linearly extending in a first direction and shorter conduit portions 154 linearly extending in a second direction vertically aligned to the first direction, which are connected by curved conduit portions 156. When orienting the elongated cartridge 142 in vertical direction with respect to gravity, the longer conduit portions 152 extend in vertical direction.

Specifically, the pressure transmission liquid conduit 124 includes a first longer portion 158 which, being linearly aligned with the pipetting tip 104, extends from the pipetting tip 104 to the beginning of the first curved conduit portion 160 of the pressure transmission liquid conduit 124. The first longer portion 158 of the pressure transmission liquid conduit 124 and the pipetting tip 104 may mutually define a fluid sample conduit 162 for receiving fluid samples aspirated through the pipetting tip 104. When vertically orienting the elongated cartridge 142 (i.e., vertically orienting the pipetting tip 104), the fluid sample conduit 162 extends in the direction of fall.

When using liquid pressure transmission liquid, the vertically oriented fluid sample conduit 162 causes microscopic (solid) particles such as magnetic beads contained in fluid samples to drop down by the pure action of gravity, which advantageously avoids diffusing the particles into the pressure transmission liquid. For this reason, fluid samples containing microscopic particles typically are only aspirated into this vertically oriented fluid sample conduit 162 but not beyond, i.e., such fluid samples are not aspirated into the first curved conduit portion 160. Otherwise, fluid samples free of microscopic particles can also be aspirated beyond the first longer portion 158 of the pressure transmission liquid conduit 124. In the latter case, one or more longer conduit portions 152, one or more shorter conduit portions 154, one or more curved conduit portions 156, and the pipetting tip 104 may mutually define a fluid sample conduit 162.

A pipetting module 102 with such an internal fluid sample conduit 162 has a significant advantage. When pipetting is controlled in a way that other fluids than pressure transmission liquid are only aspirated into this fluid sample conduit 162, this will be the only place where contamination can occur. In practice, substances such as, e.g., proteins, contained in sample fluids, are adsorbed on the inner walls of the conduit. During subsequent pipetting processes such adsorbed substances are partially desorbed and contaminate dispensed fluids. In practice, contaminated tubings have to be replaced after some months, the time very much depending on the type of sample fluids and intensity of usage. Replacement of the tubings can be quite cumbersome and often needs a service technician. Due to the modular pipetting unit of the present disclosure this service action can be simplified very much because the only item to be exchanged is the detachable pipetting module 102, which incorporates the tubing to be exchanged.

Further modular pipetting modules 102 are provided, which have at least one winding of the pressure transmission liquid conduit 124 inside the pipetting module 102. By this, the volume capacity of the pipetting module 102 is increased and pipetting processes are not so restricted by the requirement that fluid samples are only aspirated into the pipetting module 102 but not beyond.

Having a fluid conduit inside the cartridge 142 of the modular pipetting module 102 further has the advantage that the conduits are protected against mechanical stress and ultraviolet radiation. Further, the cartridge 142 may be formed as a metal housing that provides protection against electromagnetic radiation so that detections of e.g., phase boundaries, liquid level detection are not disturbed.

In order to enable pipetting of sufficiently large volumes of fluid samples, the first longer portion 158 of the pressure transmission liquid conduit 124 typically has a length of more than 5 cm and may, e.g., have a length in a range of from 5 to 25 cm to achieve sufficiently strong inhibition of particle diffusion. Furthermore, the first longer portion 158 of the pressure transmission liquid conduit 124 typically has a diameter of less than 3 mm.

As shown in FIG. 1, when installed into the cellular analyzer 100, each pipetting module 102 is vertically oriented with respect to gravity, which results in vertically oriented fluid sample conduits 162 for accommodating fluid samples aspirated through the pipetting tips 104, so that microscopic particles contained in the fluid samples are caused to drop down by the action of gravity. As illustrated in FIG. 1, in the cellular analyzer 100, the pipetting modules 102 are serially aligned with respect to each other, wherein a distance in-between adjacent pipetting tips 104 is chosen to correspond to a distance in-between adjacent cavities or vessels of a plurality of equally-distanced cavities or vessels containing the fluid samples to be transferred. The cellular analyzer 100 of FIG. 1 may thus advantageously be used for the pipetting of fluid samples contained in equally-distanced cavities such as the wells of multi-well plates.

The pipetting module 102 may further include a sensor arrangement (not shown in detail) comprising plural sensors electrically connected to a controller (not illustrated) for controlling of pipetting operations. The pipetting module 102 is provided with an electric connector 164 to be connected with electric lines for connecting the pipetting module 102 with the controller. Sensors of the sensor arrangement are adapted for sensing of physical parameters, in particular during pipetting of fluids, such as fluid flow rate and fluid pressure in the fluid sample conduit 162, or a distance between the pipetting tip 104 and another object such as a work-surface. This enables to either control and/or monitor pipetting processes based on the sensor signals.

The cellular analyzer 100 further includes a controller 166 for controlling of pipetting of fluids of each of the pipetting channels 116. In that, the controller is configured to control pipetting of each of the pipetting channels 116 in such a way that each pipetted volume of fluids is smaller than a volume of the fluid sample conduit 162 of the pipetting module 102 concerned.

As the cellular analyzer 100 is used to analyze liquid cellular samples, it is not possible to use any pressure transmission liquid such as pure or deionized water, for the reasons above. Hence, the present disclosure suggests to use a specific pressure transmission liquid 122 as will be described below. The pressure transmission liquid 122 comprises an aqueous solution of at least one substance. The solution has isotonic and substantially non-conductive characteristics. For example, the at least one substance has non-ionic, zwitter-ionic or low-ionic characteristics. In any case, the solution has an osmolarity of 150 mOsm/l to 600 mOsm/l, and more typically from 200 mOsm/l to 450 mOsm/l, such as 350 mOsm/l. For example, the osmolarity may be provided by a substance that comprises a carbohydrate or a derivative thereof. Particularly, the at least one substance may comprise at least one element selected from the group consisting of: a monosaccharide, disaccharide, oligosaccharide, an ester thereof and an ether thereof. In addition or alternatively, the at least one substance comprises an amino acid. In this case, the solution has a pH at which the amino acid is substantially at its isoelectric point. The amino acid may be glycine, alanine or betaine. In addition or alternatively, the at least one substance comprises at least one element selected from the group consisting of: sorbitol, glucose, sucrose, fructose, lactose, hexose and pentose. The solution may further have an electrical conductivity of not more than 2 mS/cm, more typically not more than 1 mS/cm, and most typically not more than 0.5 mS/cm, such as 0.40 mS/cm.

If applicable, the at least one substance may comprise ionic components. The ionic components may comprise at least one element selected from the group consisting of: ions of alkali or earth alkali metals, halides, copper phosphates, sulfates, borates, nitrates, carbonates, azide, amino-acids, and ions of organic acids, benzoate, and salts of EDTA. The solution may further comprise at least one antimicrobial preservative. The antimicrobial preservative may be sodium azide or phenoxy-ethanol.

An exact composition of the solution may be 25 g/l to 110 g/l glucose, e.g., 55 g/l glucose; 25 g/l to 110 g/l sorbitol, e.g., 55 g/l sorbitol; 50 g/l to 205 g/l sucrose, e.g., 92.5 g/l sucrose; and an electrical conductivity of not more than 2 mS/cm. Another alternative applicable solution may comprise 10 g/l to 45 g/l glycine, e.g., 22 g/l glycine, at a pH of 6.0 and an electrical conductivity of not more than 2 mS/cm.

Hereinafter a method for analyzing a liquid cellular sample using the cellular analyzer 100 will be described. Basically the method comprises the following steps. The pipetting tip 104 is positioned at or in the vicinity of the liquid cellular sample by means of the automated positioning device 106. The term "at" or "in the vicinity of the liquid cellular sample" is to be understood in that the pipetting tip 104 is arranged or positioned at a position where the pipetting tip 104 is allowed to detect a liquid level of the liquid cellular sample. For example, the pipetting tip 104 is positioned above the liquid cellular sample. Then, a liquid level of the liquid cellular sample is detected by means of the capacitive liquid level sensor 118 in order to prevent aspiration of air into the pipetting tip 104. For example, the pipetting tip 104 is moved or lowered by means of the automated positioning device 106 so as to contact the liquid level of the liquid cellular sample. Subsequently, the pipetting tip 104 is immersed into the liquid cellular sample. Finally, a negative pressure is transferred to the pipetting tip 104 by means of the pump 128 so as to aspirate an aliquot of the liquid cellular sample into the pipetting tip 104.

Accordingly, generating a liquid pressure transmission liquid flow directed to the pressure transmission liquid reservoir 120 generates a negative pressure in the pipetting tip 104 to thereby aspirate fluid into the fluid sample conduit 162. On the other hand, generating a liquid pressure transmission liquid flow directed to the pipetting tip 104 generates a positive pressure in the pipetting tip 104 to thereby dispense fluid contained in the fluid sample conduit 162.

The pressure transmission liquid valve 138 is operatively coupled to the pump 128 and is opened when a pumping operation of the pump 128 is performed to enable liquid pressure transmission liquid flow through the pressure transmission liquid conduit 124 and is closed when the pump 128 is not operated to close the pressure transmission liquid conduit 124. The pressure sensor 140 is used for sensing of pressure transmission liquid pressure in the pressure transmission liquid conduit 124.

The pump 128 may, e.g., be used for pipetting of fluid sample volumes in a range of from 10 µl to 1500 µl. Moreover, it may, e.g., be used for pipetting of fluid samples having flow rates in a range of from 1200 µl/sec to 72 ml/sec. Based upon such a wide range of flow rates, the pump 128 may also be used for washing the pipetting tips 104, for instance, in dispensing pressure transmission liquid through the pipetting tips 104.

While in the above embodiments the pipetting modules 102 have been shown each to be connected to a separate pump 128, in particular in case of locating the pump 128 outside the pipetting module 102, it may be typical to connect the pipetting modules 102 to a single common pump 128.

While the pipetting modules 102 have been shown to be mounted to a same transfer head 108 in the above embodiment, it may be typical to mount each of the pipetting modules 102 to a separate transfer head 108 to independently move the pipetting tips 104.

The cellular analyzer 100 further includes the controller 166 for controlling of pipetting of fluids of each of the pipetting channels 116. In that, the controller is being configured to control pipetting of each of the pipetting channels 116 in such a way that each pipetted volume of fluids is smaller than a volume of the fluid sample conduit 162 of the pipetting module 102 concerned.

Hereinafter, the principle of the liquid level detection and the effect of the pressure transmission fluid 122 according to the present disclosure will described in further detail. It is to be noted that all of the explanations below relate to a liquid level detection of human whole blood as a liquid cellular sample. Needless to say, the explanations below correspondingly apply to other kinds of liquid cellular samples such as samples including animal cells or bacterial cells. The whole blood comprises erythrocytes as cells. Whole blood is used for the explanations below as the erythrocytes may be considered as a representative type of cells in the field of the present disclosure.

Figure 4:
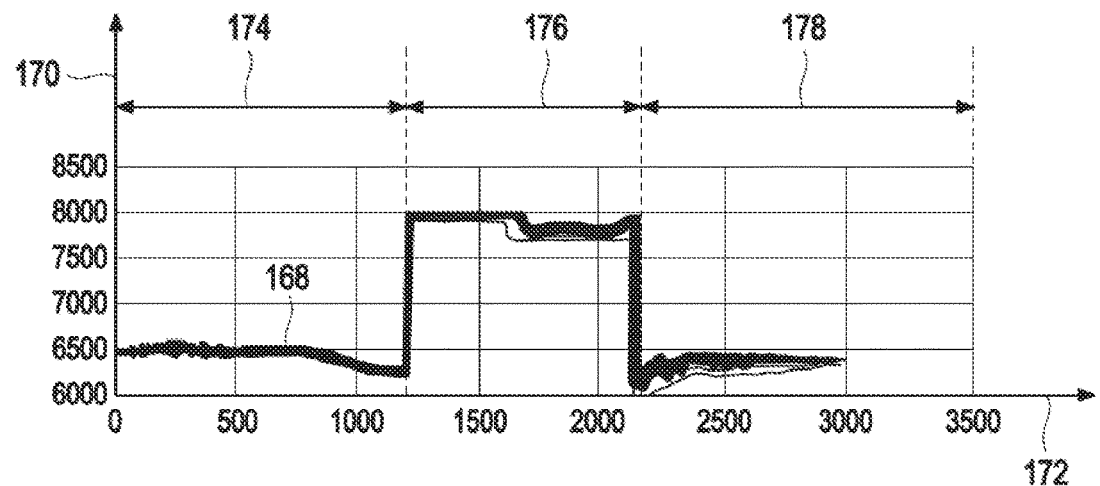
FIG. 4 shows exemplarily target curves of a capacitive signal over time.

FIG. 4 shows exemplarily target curves 168 of a capacitive signal 170 over time 172. The time 172 is indicated on the X-axis and the capacitive signal 170 is indicated on the Y-axis. The exact course of the target curves 168 is not relevant for the explanations below but only the qualitative course. The term target curve 168 is to be understood that the course thereof or a course very similar thereto allows to clearly detect the liquid level by means of variation of the capacitance at the pipetting tip 104. Hence, the target curves 168 basically comprise at least a first amplitude range 174, a second amplitude range 176, and a third amplitude range 178, wherein the second amplitude range 176 is located between the first amplitude range 174 and the third amplitude range 178. In the first amplitude range 174 and the third amplitude range 178, the pipetting tip 104 is positioned above the liquid level. In the second amplitude range 176, the pipetting tip 104 contacts the liquid level. For example, the pipetting tip 104 is immersed into the liquid in the second amplitude range 176. As can be taken from the target curves 168, the amplitude of the capacitive signal 170 is significantly greater in the second amplitude range 176 than in the first amplitude range 174 and the third amplitude range 178. Thus, the variation of the amplitude of the capacitive signal 170 allows to detect whether the pipetting tip 104 contacts the liquid level or not. Several target curves 168 are given as a process of immersing the pipetting tip 104 into the liquid and retracting the pipetting tip 104 from the liquid is repeated several times.

Figure 5:
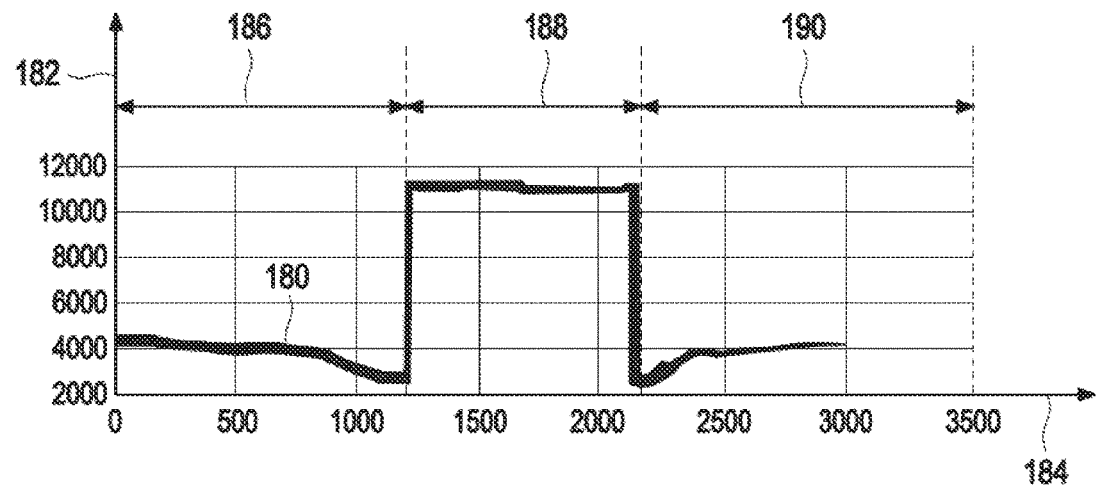
FIG. 5 shows exemplarily target curves of a resistive signal over time.

Analogously to FIG. 4, FIG. 5 shows exemplarily target curves 180 of a resistive signal 182 over time 184. It is to be noted that a detection of a resistance at the pipetting tip 104 is an additional or alternative possibility for the detection of the liquid level. The time 184 is indicated on the X-axis and the resistive signal 182 is indicated on the Y-axis. The exact course of the target curves 180 is not relevant for the explanations below but only the qualitative course. The term target curve 180 is to be understood that the course thereof or a course very similar thereto allows to clearly detect the liquid level by means of variation of the resistance at the pipetting tip 104. Hence, the target curves 180 basically comprise at least a first amplitude range 186, a second amplitude range 188, and a third amplitude range 190, wherein the second amplitude range 188 is located between the first amplitude range 186 and the third amplitude range 190. In the first amplitude range 186 and the third amplitude range 190, the pipetting tip 104 is positioned above the liquid level. In the second amplitude range 188, the pipetting tip 104 contacts the liquid level. For example, the pipetting tip 104 is immersed into the liquid in the second amplitude range 188. As can be taken from the target curves 180, the amplitude of the resistive signal 182 is significantly greater in the second amplitude range 188 than in the first amplitude range 186 and the third amplitude range 190. Thus, the variation of the amplitude of the resistive signal 182 also allows to detect whether the pipetting tip 104 contacts the liquid level or not. Several target curves 180 are given as a process of immersing the pipetting tip 104 into the liquid and retracting the pipetting tip 104 from the liquid is repeated several times.

Figure 6:
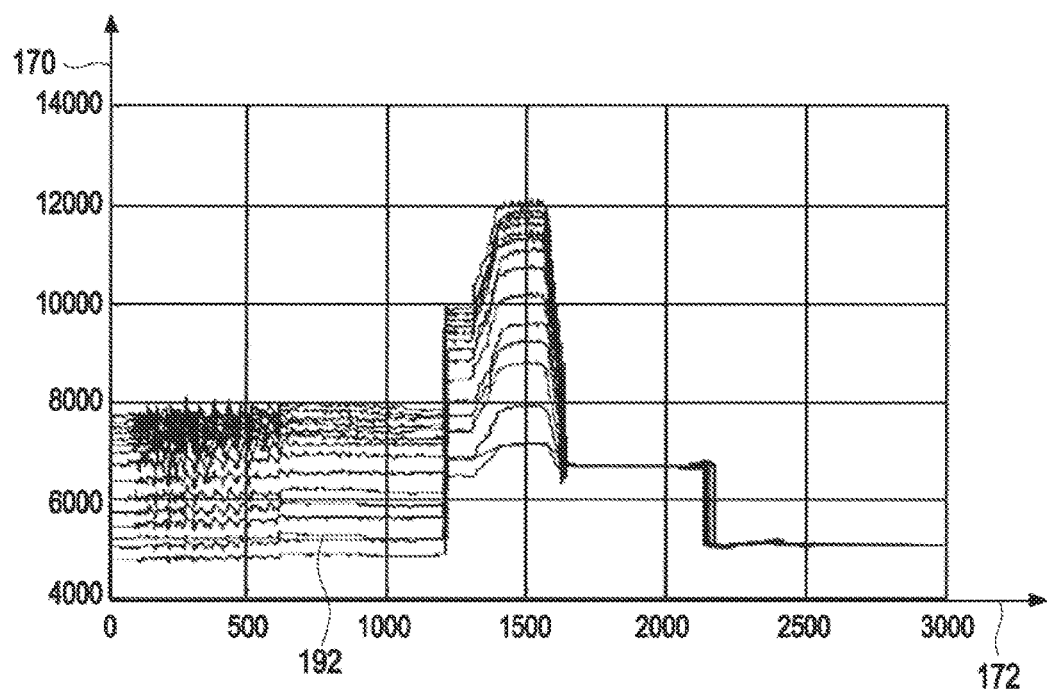
FIG. 6 shows curves of a capacitive signal over time when a conductive isotonic liquid is used as a pressure transmission liquid.

FIG. 6 shows curves 192 of a capacitive signal 170 over time 172 detected when a conductive isotonic liquid is used as a pressure transmission liquid. The time 172 is indicated on the X-axis and the capacitive signal 170 is indicated on the Y-axis. As can be taken from the curves 192, contrary to the target curves 168 shown in FIG. 4, a first amplitude range 174, a second amplitude range 176, and a third amplitude range 178 may not be clearly identified with the curves 192 as at the beginning there are amplitudes that are greater than in the middle of the detection caused by electronic noise due to the relatively high conductivity of the liquid. Several curves 192 are given as a process of immersing the pipetting tip 104 into the liquid and retracting the pipetting tip 104 from the liquid is repeated several times.

Figure 7:
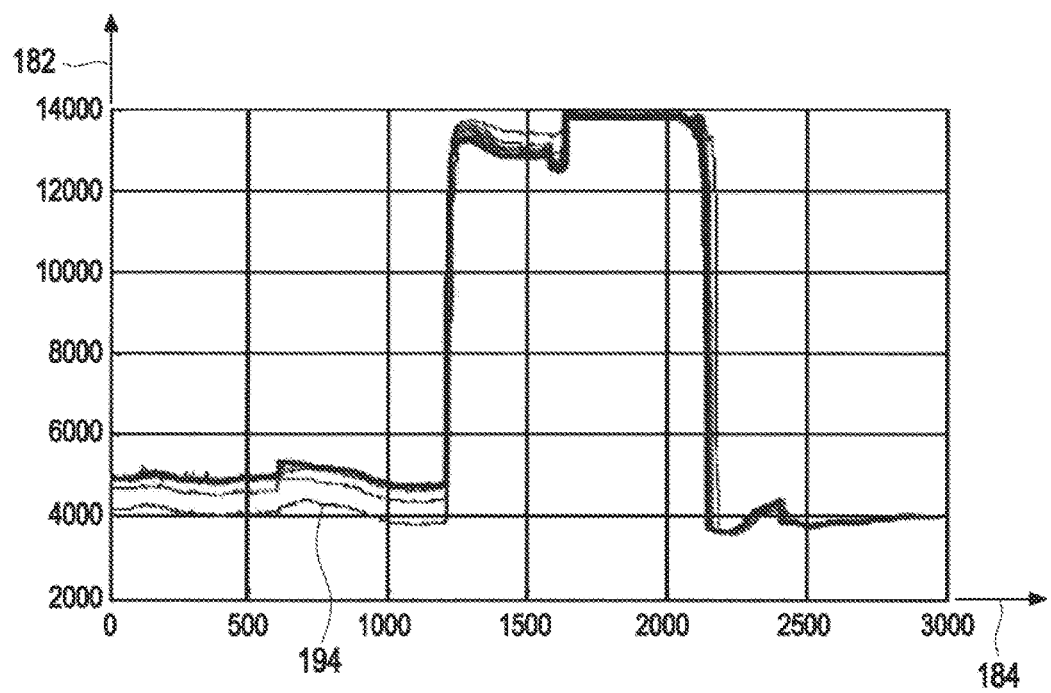
FIG. 7 shows curves of a resistive signal over time when a conductive isotonic liquid is used as a pressure transmission liquid.

Analogously to FIG. 6, FIG. 7 shows exemplarily curves 194 of a resistive signal 182 over time 184. The time 184 is indicated on the X-axis and the resistive signal 182 is indicated on the Y-axis. Even though the curves 194 basically comprise at least a first amplitude range 186, a second amplitude range 188 and a third amplitude range 190, wherein the amplitude of the resistive signal 182 is greater in the second amplitude range 188 than in the first amplitude range 186 and the third amplitude range 190, the curves vary excessively from one another such that an exact point of time when the pipetting tip 104 contacts the liquid level is not possible. Several curves 194 are given as a process of immersing the pipetting tip 104 into the liquid and retracting the pipetting tip 104 from the liquid is repeated several times.

Figure 8:
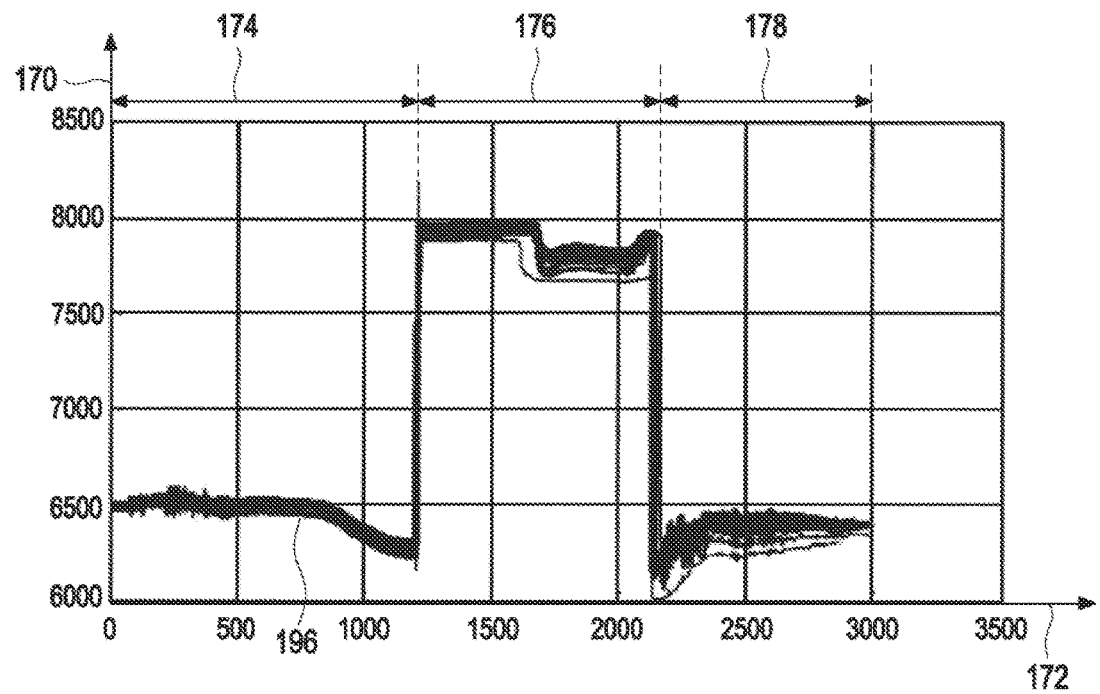
FIG. 8 shows curves of a capacitive signal over time when deionized water is used as a pressure transmission liquid.

FIG. 8 shows curves 196 of a capacitive signal 170 over time 172 detected when deionized water is used as a pressure transmission liquid. The time 172 is indicated on the X-axis and the capacitive signal 170 is indicated on the Y-axis. As can be taken from FIG. 8, the curves 196 are very similar to the target curves 168 shown in FIG. 4. Hence, the curves 196 basically comprise at least a first amplitude range 174, a second amplitude range 176 and a third amplitude range 178. As can be taken from the curves 196, the amplitude of the capacitive signal 170 is significantly greater in the second amplitude range 176 than in the first amplitude range 174 and the third amplitude range 178. Thus, the variation of the amplitude of the capacitive signal 170 allows to detect whether the pipetting tip 104 contacts the liquid level or not. However, deionized water may not be used in the field of the present disclosure as deionized water is hypotonic and causes lysis of the cells of the cellular samples. Several curves 196 are given as a process of immersing the pipetting tip 104 into the liquid and retracting the pipetting tip 104 from the liquid is repeated several times.

Figure 9:
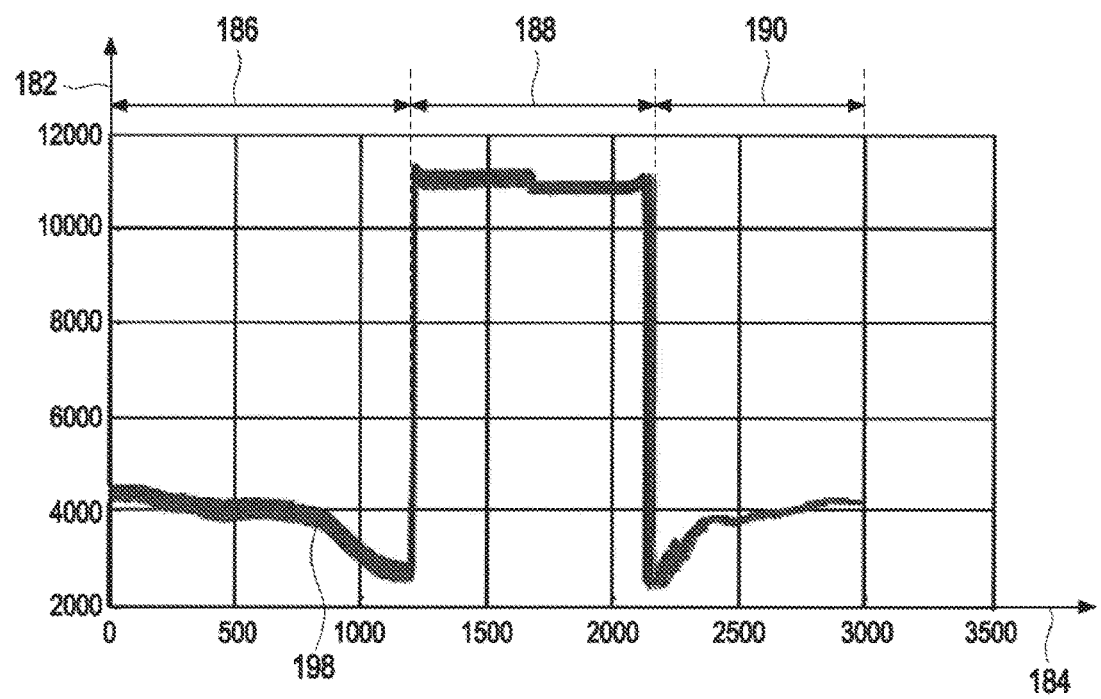
FIG. 9 shows curves of a resistive signal over time when deionized water is used as a pressure transmission liquid.

Analogously to FIG. 8, FIG. 9 shows exemplarily curves 198 of a resistive signal 182 over time 184. The time 184 is indicated on the X-axis and the resistive signal 182 is indicated on the Y-axis. As can be taken from FIG. 9, the curves 198 are very similar to the target curves 180 shown in FIG. 5. Hence, the curves 198 basically comprise at least a first amplitude range 186, a second amplitude range 188 and a third amplitude range 190. As can be taken from the curves 198, the amplitude of the resistive signal 182 is significantly greater in the second amplitude range 188 than in the first amplitude range 186 and the third amplitude range 190. Thus, the variation of the amplitude of the resistive signal 182 allows to detect whether the pipetting tip 104 contacts the liquid level or not. However, this liquid level detection method in combination with deionized water may not be used in the field of the present disclosure as deionized water is hypotonic and causes lysis of the cells of the cellular samples. Several curves 198 are given as a process of immersing the pipetting tip 104 into the liquid and retracting the pipetting tip 104 from the liquid is repeated several times.

Figure 10:
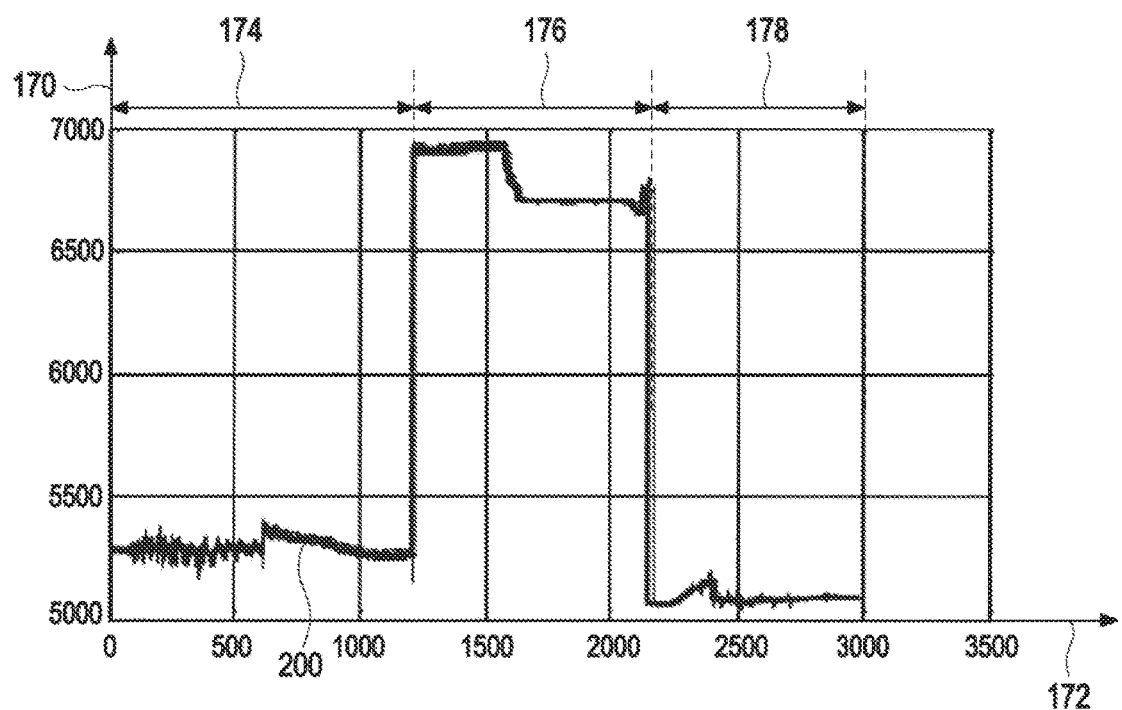
FIG. 10 shows curves of a capacitive signal over time when a pressure transmission liquid according to the present disclosure is used.

FIG. 10 shows curves 200 of a capacitive signal 170 over time 172 detected when the pressure transmission liquid 122 according to the present disclosure is used as a pressure transmission liquid. The time 172 is indicated on the X-axis and the capacitive signal 170 is indicated on the Y-axis. As can be taken from FIG. 10, the curves 200 are very similar to the target curves 168 shown in FIG. 4. Hence, the curves 200 basically comprise at least a first amplitude range 174, a second amplitude range 176 and a third amplitude range 178. As can be taken from the curves 200, the amplitude of the capacitive signal 170 is significantly greater in the second amplitude range 176 than in the first amplitude range 174 and the third amplitude range 178. Thus, the variation of the amplitude of the capacitive signal 170 allows to detect whether the pipetting tip 104 contacts the liquid level or not. Further, as the pressure transmission liquid 122 has isotonic characteristics, it may be used in the field of the present disclosure as it does not cause electric noise and lysis of the cells of the cellular samples. Several curves 200 are given as a process of immersing the pipetting tip 104 into the liquid and retracting the pipetting tip 104 from the liquid is repeated several times.

Figure 11:
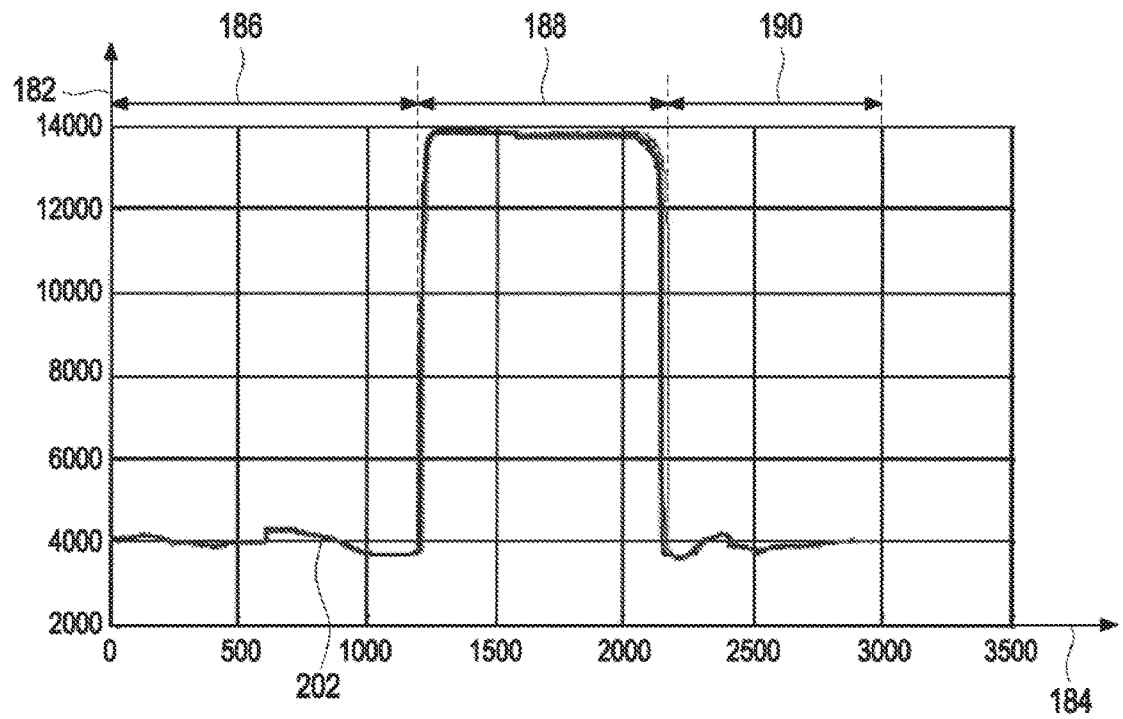
FIG. 11 shows curves of a resistive signal over time.

Analogously to FIG. 10, FIG. 11 shows exemplarily curves 202 of a resistive signal 182 over time 184. The time 184 is indicated on the X-axis and the resistive signal 182 is indicated on the Y-axis. As can be taken from FIG. 11, the curves 202 are very similar to the target curves 180 shown in FIG. 5. Hence, the curves 202 basically comprise at least a first amplitude range 186, a second amplitude range 188 and a third amplitude range 190. As can be taken from the curves 198, the amplitude of the resistive signal 182 is significantly greater in the second amplitude range 188 than in the first amplitude range 186 and the third amplitude range 190. Thus, the variation of the amplitude of the resistive signal 182 allows to detect whether the pipetting tip 104 contacts the liquid level or not. Further, as the pressure transmission liquid 122 has isotonic characteristics, it may be used in the field of the present disclosure as it does not cause electric noise and lysis of the cells of the cellular samples. Several curves 202 are given as a process of immersing the pipetting tip 104 into the liquid and retracting the pipetting tip 104 from the liquid is repeated several times.

A method for detecting whether lysis of the cells of the cellular samples occurs or not will be described below with reference to human erythrocytes. A cellular sample of 50 µl whole blood is mixed with 950 µl of the pressure transmission liquid 122. The mixture is incubated with a duration of 5 minutes at room or ambient temperature. Cells that have not lysed are separated by means of centrifugation with a duration of 5 minutes with an acceleration of 450 g. Free hemoglobin is detected in the supernatant resulting from the centrifugation process. Any lysis occurred may be qualitatively detected by means of the color of the supernatant. If the supernatant is red, then lysis of the cells has occurred. Using any isotonic liquids such as the pressure transmission liquid according to the present disclosure will result in that the supernatant will be colorless indicating that lysis of the cells has not occurred. Any further suitable methods for detecting whether lysis of the cells of the cellular samples occurs or not, such as photometric hemoglobin detection or the like, are known to the skilled person and will not be described in detail herein. In the examples described above, hemolysis was observed visually in the case of deionized water as pressure transmission liquid, but not in the case of a conductive isotonic pressure transmission liquid or a pressure transmission liquid according to the disclosure. Thus, the pressure transmission liquid according to the present disclosure has been shown to allow for both of reliable capacitive liquid level detection and lysis-free pipetting of cellular samples.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may all refer to a situation in which, besides B, no other element is present in A (i.e., a situation in which A solely and exclusively consists of B) and to a situation in which, besides B, one or more further elements are present in entity A, such as element C, elements C and D, or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, notwithstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure, and without any restriction regarding the possibility of combining the features introduced in such way with other optional or non-optional features of the disclosure.

It is further noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will also be apparent to those skilled in the art that various modifications and variations can be made to the embodiments described herein without departing from the spirit and scope of the claimed subject matter. Thus, it is intended that the specification cover the modifications and variations of the various embodiments described herein provided such modifications and variations come within the scope of the appended claims and their equivalents.

LIST OF REFERENCE NUMBERS 100 cellular analyzer
102 pipetting module
104 pipetting tip
106 automated positioning device
108 transfer head
110 vertical guiding rail
112 sliding carriage
114 horizontal guiding rail
116 pipetting channel
118 capacitive liquid level sensor
120 pressure transmission liquid reservoir
122 pressure transmission liquid
124 pressure transmission liquid conduit
126 fluidic connector
128 pump
130 guiding chain
132 chain link
134 first inlet/outlet port
136 second inlet/outlet port
138 pressure transmission liquid valve
140 pressure sensor
142 cartridge
144 corrugated outer surface
146 cavity
148 guiding face
150 inner wall
152 longer conduit portion
154 shorter conduit portion
156 curved conduit portion
158 first longer portion
160 first curved conduit portion
162 fluid sample conduit
164 electric connector
166 controller
168 target curve
170 capacitive signal
172 time
174 first amplitude range
176 second amplitude range
178 third amplitude range
180 target curve
182 resistive signal
184 time
186 first amplitude range
188 second amplitude range
190 third amplitude range
192 curve
194 curve
196 curve
198 curve
200 curve
202 curve

What is claimed is:

1. A system for transferring a liquid cellular sample for analysis by a cellular analyzer comprising:
    a pipetting module having a pipetting tip, the pipetting module comprising a fluid sample conduit configured for receiving fluid samples aspirated through the pipetting tip;
    an automated positioning device configured for positioning the pipetting module;
    a vessel for receiving a liquid cellular sample to be analyzed;
    a capacitive liquid level sensor configured for detecting the liquid level of a liquid cellular sample received within the vessel;
    a reservoir comprising a pressure transmission liquid comprising an aqueous solution of at least one substance, wherein the aqueous solution has an osmolarity of 150 mOsm/l to 600 mOsm/l, and has an electrical conductivity of not more than 2 mS/cm;
    a pressure transmission liquid conduit fluidically connecting the fluid sample conduit of the pipetting tip with the pressure transmission liquid reservoir; and
    a pump coupled with the pressure transmission liquid conduit and configured to generate a pressure transmission liquid flow directed to the reservoir to aspirate a liquid cellular sample into the fluid sample conduit, and to generate a pressure transmission liquid flow direct to the pipetting tip to dispense liquid cellular sample from the pipetting tip.

2. The system according to claim 1, wherein the pressure transmission liquid conduit has at least one winding inside the pipetting module.

3. A method for transferring a liquid cellular sample for analysis by a system according to claim 1, the method comprising:
- detecting a liquid level of a liquid cellular sample received within the vessel,
- immersing the pipetting tip into the liquid cellular sample, and
- transferring a negative pressure to the pipetting tip so as to aspirate an aliquot of the liquid cellular sample into the pipetting tip.

4. The system, according to claim 1, wherein the aqueous solution has n osmolarity of 200 mOsm/l to 450 mOsm/l.

5. The system according to claim 4 wherein the at least one substance comprises a carbohydrate or a carbohydrate derivative.

6. The system according to claim 5, wherein the carbohydrate or carbohydrate derivative is selected from the group consisting of a monosaccharide, a disaccharide, and an oligosaccharide.

\* \* \* \* \*